(12) United States Patent
Gerlitz et al.

(10) Patent No.: US 10,898,723 B2
(45) Date of Patent: Jan. 26, 2021

(54) SCANNING MECHANISM AND TREATMENT METHOD FOR LLLT OR OTHER LIGHT SOURCE THERAPY DEVICE

(75) Inventors: Yonatan Gerlitz, Herzliya (IL); Michael Schlosser, Haifa (IL)

(73) Assignee: Michael Schlosser, Haifa (IL)

(*) Notice: Subject to any disclaimer, the term of this patent is extended or adjusted under 35 U.S.C. 154(b) by 0 days.

(21) Appl. No.: 13/006,969

(22) Filed: Jan. 14, 2011

(65) Prior Publication Data
US 2011/0178583 A1    Jul. 21, 2011

Related U.S. Application Data

(60) Provisional application No. 61/295,051, filed on Jan. 14, 2010.

(51) Int. Cl.
*A61N 5/06* (2006.01)
*A61N 5/067* (2006.01)
*A61B 18/20* (2006.01)

(52) U.S. Cl.
CPC ...... *A61N 5/0616* (2013.01); *A61B 2018/207* (2013.01); *A61B 2018/20351* (2017.05); *A61B 2018/20355* (2017.05); *A61N 2005/067* (2013.01); *A61N 2005/0629* (2013.01); *A61N 2005/0643* (2013.01); *A61N 2005/0651* (2013.01); *A61N 2005/0659* (2013.01)

(58) Field of Classification Search
CPC .................................................. A61N 5/0616
USPC ........................................................ 607/88–90
See application file for complete search history.

(56) References Cited

U.S. PATENT DOCUMENTS

| 6,371,637 | B1 | 4/2002 | Atchinson et al. |
| 6,872,221 | B2* | 3/2005 | Lytle ............................... 607/89 |
| 2002/0173833 | A1 | 11/2002 | Korman et al. |
| 2002/0188334 | A1 | 12/2002 | Carlgren |
| 2004/0158301 | A1 | 8/2004 | Tucek et al. |
| 2006/0095099 | A1 | 5/2006 | Shanks et al. |
| 2006/0206173 | A1 | 9/2006 | Gertner et al. |
| 2006/0224218 | A1 | 10/2006 | Tucek et al. |
| 2007/0121069 | A1* | 5/2007 | Andersen et al. ............ 351/221 |
| 2007/0185552 | A1* | 8/2007 | Masotti et al. ................ 607/89 |
| 2008/0058783 | A1* | 3/2008 | Altshuler et al. ................. 606/9 |
| 2009/0105791 | A1 | 4/2009 | McGinnis et al. |

(Continued)

FOREIGN PATENT DOCUMENTS

| JP | S6141471 | 2/1986 |
| JP | 2002306508 | 10/2002 |

(Continued)

OTHER PUBLICATIONS

Ehlers, Bodo. Zoom optics maximize diode-lser efficiency. Feb. 1, 2000. Laser Focus World. http://business.highbeam.com/418602/article-1G1-64191079/zoom-optics-maximize-diodelaser-efficiency.*

(Continued)

*Primary Examiner* — John R Downey
(74) *Attorney, Agent, or Firm* — Randall Danskin, P.S.

(57) ABSTRACT

A scanning mechanism to scan a light source, such as a low-level laser, to create a desirable energy distribution on a treatment area. The light source may include multiple light beam generators, each having a different wavelength and each having a different energy distribution. The scanning mechanism can be programmable to scan in different patterns in accordance with a desired treatment.

23 Claims, 5 Drawing Sheets

(56) References Cited

U.S. PATENT DOCUMENTS

2010/0053070 A1* 3/2010 Tsai et al. ............... 345/156
2010/0324426 A1* 12/2010 Tucek et al. ............. 600/476

FOREIGN PATENT DOCUMENTS

| JP | 200379752 | 3/2003 |
| JP | 200534102 | 9/2009 |
| JP | 2010506624 | 3/2010 |
| WO | WO2004105873 | 12/2004 |
| WO | WO2006125367 | 11/2006 |
| WO | WO2008046015 | 4/2008 |
| WO | WO2008124839 | 10/2008 |

OTHER PUBLICATIONS

Patent Cooperation Treaty, International Search Authority, International Search Report and Written Opinion, dated Aug. 17, 2011, International Application No. PCT/IB2011/000206.
European Patent Office, Extended Eruopean Search Report for EP Application No. 11732715.5 dated Jun. 26, 2013; dated Jun. 26, 2013.
Eurasian Patent Organization, Office Action for EA Application No. 201270688/31 dated Sep. 6, 2013, dated Sep. 6, 2013.
Japanese Patent Office; Office Action for JP Appl No. 2012-548499 dated Sep. 16, 2014, dated Sep. 16, 2014.
Japanese Patent Office; Final Office Action for JP Application No. 2012-548499 dated Jun. 15, 2015, dated Jun. 15, 2015.

* cited by examiner

SCANNING MECHANISM AND TREATMENT METHOD FOR LLLT OR OTHER LIGHT SOURCE THERAPY DEVICE

RELATED APPLICATIONS

The present application claims the benefit of priority under 35 U.S.C. § 119 to U.S. Provisional Application No. 61/295,051 filed Jan. 14, 2010, entitled Scanning Mechanism and Treatment Method for LLLT or Another Light Source Therapy Device, the disclosure of which is hereby incorporated herein by reference in its entirety.

BACKGROUND OF THE DISCLOSURE

Field of the Disclosure

The present disclosure relates generally to low-level laser therapy and, more specifically, to a mechanical scanning device for use in low-level laser therapy applications.

Description of the Related Art

The use of light for treating people and animals is well known. Since the early history of mankind people have used the light from the sun to help cure ailments. In the mid-twentieth century attempts were made to use concentrated light for treating wounded soldiers in World War II.

More recently, the use of laser light in therapy has been shown to reduce pain, induce anti-inflammatory activity, induce healing processes and induce skin rejuvenation. The laser, which is based on the quantum phenomenon of stimulated emission, provides an excellent source of concentrated light for treating patients. The laser allows the use of a selected intensity, monochromatic, and essentially coherent light. This has been found to be effective in treating people for various ailments.

Low-level laser therapy ("LLLT") is the application of visible red or near-infrared light emitted from a low power laser for therapeutic purposes. At present, there are several variations of LLLT devices, such as devices having one light source which covers a small area of the body, shower devices which contain a two or more light sources and therefore cover a larger body area, and cluster devices which combine a variety of light sources, having different wave lengths and energy distributions. On many occasions, in order to cover a larger area, the beams generated by the light source have divergent angles and do not remain coherent.

Many treatments with LLLT devices or other light sources require the treatment of a wide or large area of the human body rather than a small area or specific spot. Typically, a therapist scans the treatment area by moving the LLLT device or other light source device or probe by hand. The results of scanning in such a way are limited as the treatment does not always cover the desired area properly with the required light and/or energy dose to each treatment area unit.

SUMMARY

The present disclosure provides an apparatus and method for treating an area with a low-level laser or another light source or energy source, device so the distribution of the light or other energy on the treatment area can be custom designed for a particular treatment procedure and repeated in the same manner for all similar treatments. As used herein, the term "light source" is used to designate the source of an energy beam or beams which provide energy to the treatment area during an LLLT procedure. While light energy is used as an example in the present disclosure, the term "light source" may refer to any suitable energy source such as an ultrasonic energy source, for example. Also, the term "scanning" or "scanned" as used herein includes all motions, such as spinning, rotating, vibrating, sliding, oscillating, eccentric motion, and the like.

In one embodiment according to the present disclosure, an apparatus includes a light source and a scanning mechanism attached to the light source and adapted to impart a desired motion to the light source. The scanning mechanism may be an electric motor rotating the light beam or beams generated by the light source to provide a desired energy distribution pattern on a treatment area or to cover a wide treatment area, applying different light sources and different wavelengths, each with a different energy distribution on each of a plurality of selected treatment areas. The light source may include a laser, such as a laser diode, for example. In another embodiment, the light source may include two or more light sources, each light source generating a light beam having a different wavelength, thus providing a composite coherent light beam.

In another embodiment according to the present disclosure, a method of treatment includes generating a light beam and scanning the light beam across a treatment area in a predetermined pattern for providing a desired energy distribution pattern at a treatment area. Scanning the light beam may include rotating a light source which generates the light beam or, alternatively, moving the light source in two dimensions to scan the light beam or beams across a wide treatment area. In another embodiment the light source may be a cluster of light sources wherein the scanning the light source provides sequential irradiation of a plurality of unit areas of a treatment area with each of the two or more light beams providing an energy distribution corresponding to each of the two or more light beams to each of the plurality of unit areas In another embodiment of the present disclosure, an apparatus including a support frame is provided having a plurality of mounting points formed therein, and at least one light source module mounted on the support frame at one or more of the mounting points. The support frame may be a semi-rigid belt or web having a plurality of light source modules mounted at selected ones of the mounting points to form a predetermined energy distribution pattern at the surface of a treatment area. The apparatus includes a controller and power supply coupled to the support frame for providing control signals and power to the array of light source modules.

These and other embodiments of the present disclosure will be discussed more fully in the detailed description. The features, functions, and advantages can be achieved independently in various embodiments of the claimed invention, or may be combined in yet other embodiments. Like reference numbers and designations in the various drawings indicate like elements.

DETAILED DESCRIPTION

In the following description, reference is made to the accompanying drawings that form a part thereof, and in which is shown by way of illustration specific exemplary embodiments in which the disclosure may be practiced. These embodiments are described in sufficient detail to enable those skilled in the art to practice the disclosure, and it is to be understood that modifications to the various disclosed embodiments may be made, and other embodiments may be utilized, without departing from the spirit and scope of the present disclosure. The following detailed description is, therefore, not to be taken in a limiting sense.

Figure 1:
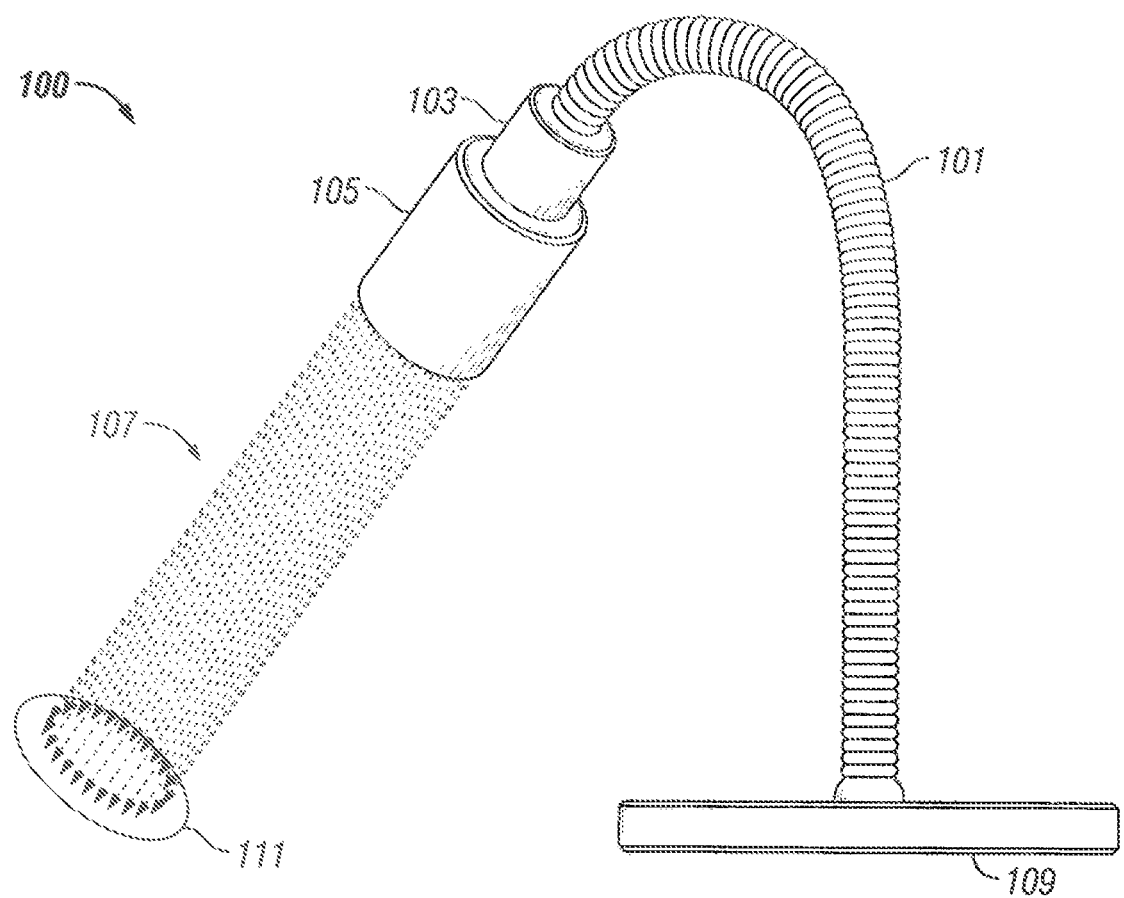
FIG. 1 is a perspective view of a rotating mechanism to create a circular energy distribution on a treated area according to the present disclosure.

Referring to FIG. 1, a scanning mechanism 100 to create a circular energy distribution on a treated area according to the present disclosure is shown. A flexible arm 101 is attached to a base 109 at one end thereof. A scanning mechanism 103, such as an electric motor, for example, is attached at the opposite end of the flexible arm 101 and is supported by the arm 101. In some embodiments, the flexible arm 101 comprises a flexible tube wherein electrical wiring and power cables (not shown) may be routed. A source 105 is attached to the scanning mechanism 103. Scanning mechanism 103 is adapted to impart motion to the light source 105 in a desired manner. For example, in one embodiment, scanning mechanism 103 rotates the light source 105 about the axis of the light beam 107 thereby rotating the light beam 107 about its axis. Light source 105 may be a low-level laser or other suitable light source which generates light beam 107 to illuminate a desired area 111 to be treated. Scanning mechanism 103 rotates or otherwise moves the light source 105 such that the treatment area 111 is scanned by the light beam 107 to provide a desired energy distribution over the treatment area. As used herein, the term "light source" is used to designate the source of an energy beam or beams which provide energy to the treatment area during an LLLT procedure. While light energy is used as an example in the present disclosure, the term "light source" may refer to any suitable energy source such as an ultrasonic energy source, for example. Also, the term "scanning" or "scanned" as used herein includes all motions, such as spinning, rotating, vibrating, sliding, oscillating, eccentric motion, and the like.

In one embodiment, light source 105 comprises a low-level laser that provides as output an elongated monochromatic coherent laser beam 107 that is collimated by a lens (not shown) directly from a laser diode embedded in light source 105. The effects of LLLT appear to be limited to a specified set of wavelengths of laser emissions. The typical wavelength is in the range 600-1000 nm (red to near infrared), although research shows that some wavelengths outside this range may also be useful. The typical laser average power used in LLLT treatment is in the range of 1-500 mW. While some high-peak-power lasers in the range of 1-30 W may be used, a short pulse width limits the power at the treatment area. The standard laser diode beam typically has a divergence of about 5-7 degrees along its width and about 30 to 40 degrees along its length. Typically, a lens is utilized to correct the beam to a narrow beam. In an exemplary embodiment of the disclosure, the resulting elongated beam 107 is essentially coherent having a light beam with an essentially common phase as accepted for laser diode emission for use in LLLT. In some embodiments, the light source 105 provides a monochromatic laser beam 107 that may be an invisible infrared beam. In some embodiments, the wavelength of laser beam 107 may be 800 to 900 nanometers (nm).

In some embodiments wherein the monochromatic laser beam 107 is an invisible infrared beam, a visible light source, for example, an LED, (not shown) may be incorporated with the light source 105 to provide a supplementary visible light beam to accompany the invisible laser beam 107. In some embodiments, the visible light beam may coincide with the invisible laser beam, or the visible light beam may illuminate an area that surrounds the laser beam 107.

In some embodiments, light source 105 may be a group or cluster of two or more light sources such as lasers, for example. Each such light source is separate and independent of the other light sources in the cluster. Each light source generates a separate beam of light at a different wavelength and may provide a beam of more or less power than each of the other light sources in the cluster. The scanning mechanism 103 may be an electric motor which slowly rotates the light source cluster, such as at 2 revolutions per minute, thus irradiating each particular unit area of the treatment area with an energy beam having a different wavelength and power to provide a desired energy distribution at any given time. Each particular unit area of the treatment area is then irradiated with each of the generated energy beams in turn over a given time period as a function of the cluster rotation rate.

Figure 2:
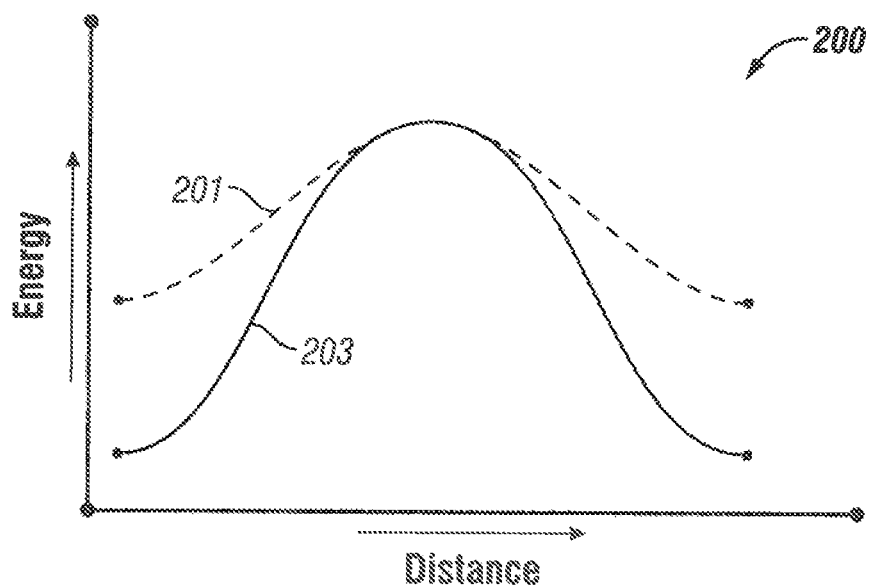
FIG. 2 is a graph illustrating a linear energy distribution of an LLLT or other light source device, and the linear energy distribution while the device is being used with a rotating mechanism according to the present disclosure.

Referring to FIG. 2, a graph illustrating a linear energy distribution of an LLLT or other light source device, and the linear energy distribution while the device is being used with a rotating mechanism according to the present disclosure is shown. Curve 201 illustrates a specific example of the energy distribution over a treated area of the light beam along the long dimension of the light beam 107, when it is not rotating. When the light beam 107 is rotating, using the motor 103, curve 203 illustrates the energy distribution created on the treated area 111 by the rotating light beam 107. Rotation of the light beam 107 produces a more uniform energy distribution across treatment area 111.

Figure 3:
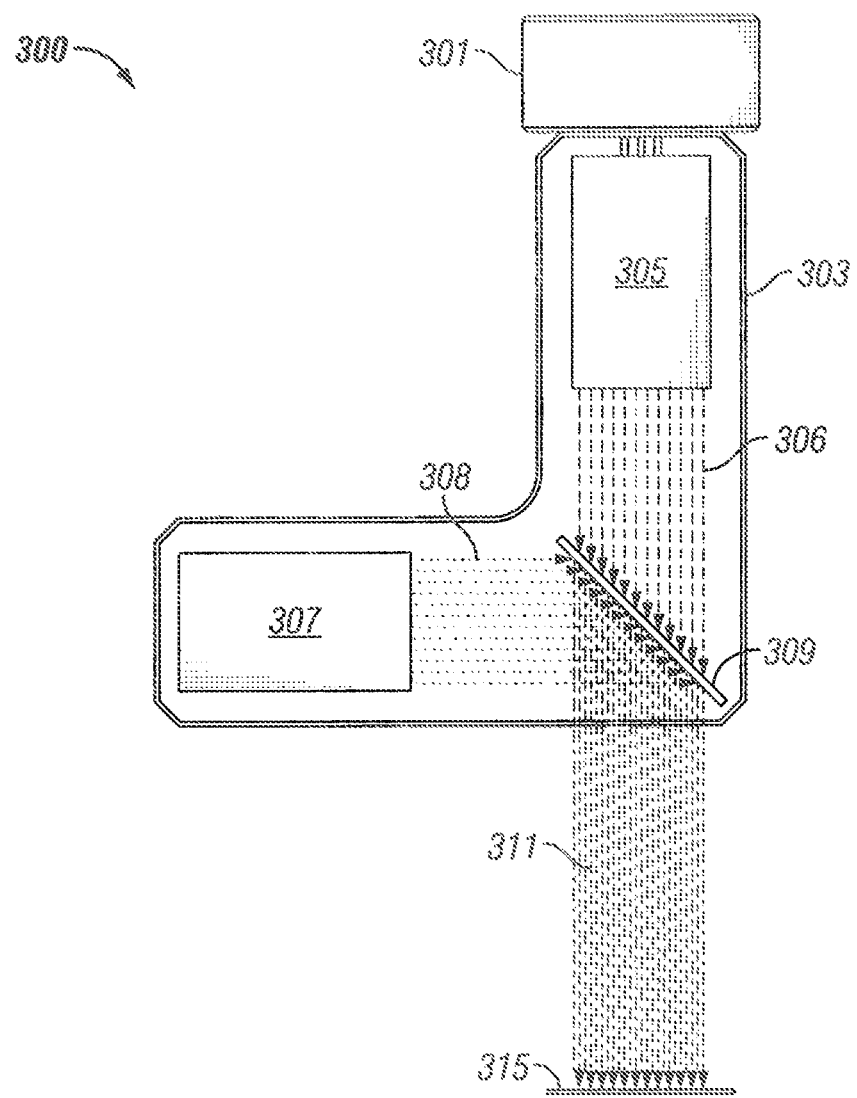
FIG. 3 is a perspective view of a scanning mechanism incorporating two light sources having different wavelengths according to the present disclosure.

Referring now to FIG. 3, a scanning mechanism incorporating two light sources generating light beams having different wavelengths according to the present disclosure is shown. A light source module 303 is attached to a motor 301. Motor 301 is adapted to impart motion to the light source module 303 in a regular, desired manner to scan a desired treatment area 315. For example, the motor 301 may rotate the light source module 303 about the axis of a light beam 311 to illuminate treatment area 315 with an energy distribution similar to that illustrated by curve 203. Two or more light sources 305, 307 of different wavelengths are mounted with the body of light source module 303. Light sources 305, 307 may be lasers, such as laser diodes, for example, each generating a laser beam 306, 308, respectively, having a different wavelength. For example, the light source module 303 may incorporate one laser 305 that emits a beam having a wavelength of 635 nm, and a second laser 307 that emits a beam having a wavelength of 808 nm. Both such lasers 305, 307 will emit a light beam which is a bright red; however since they are in the near infrared region, their light will be barely visible. The two laser beams 306, 308 are directed to an output coupler 309, such as a dichroic beam-splitter, dichroic prism or half-silvered mirror, for example. Output coupler 309 combines the two laser beams 306, 308 to provide a beam 311 that includes light of both wavelengths. In one embodiment, the lasers 305, 307 are alternately pulsed such that the beam 311 will be of only one wavelength at any given time. Alternatively, the lasers 305, 307 may be pulsed simultaneously to provide a beam 311 of both wavelengths at any given time.

Figure 4:
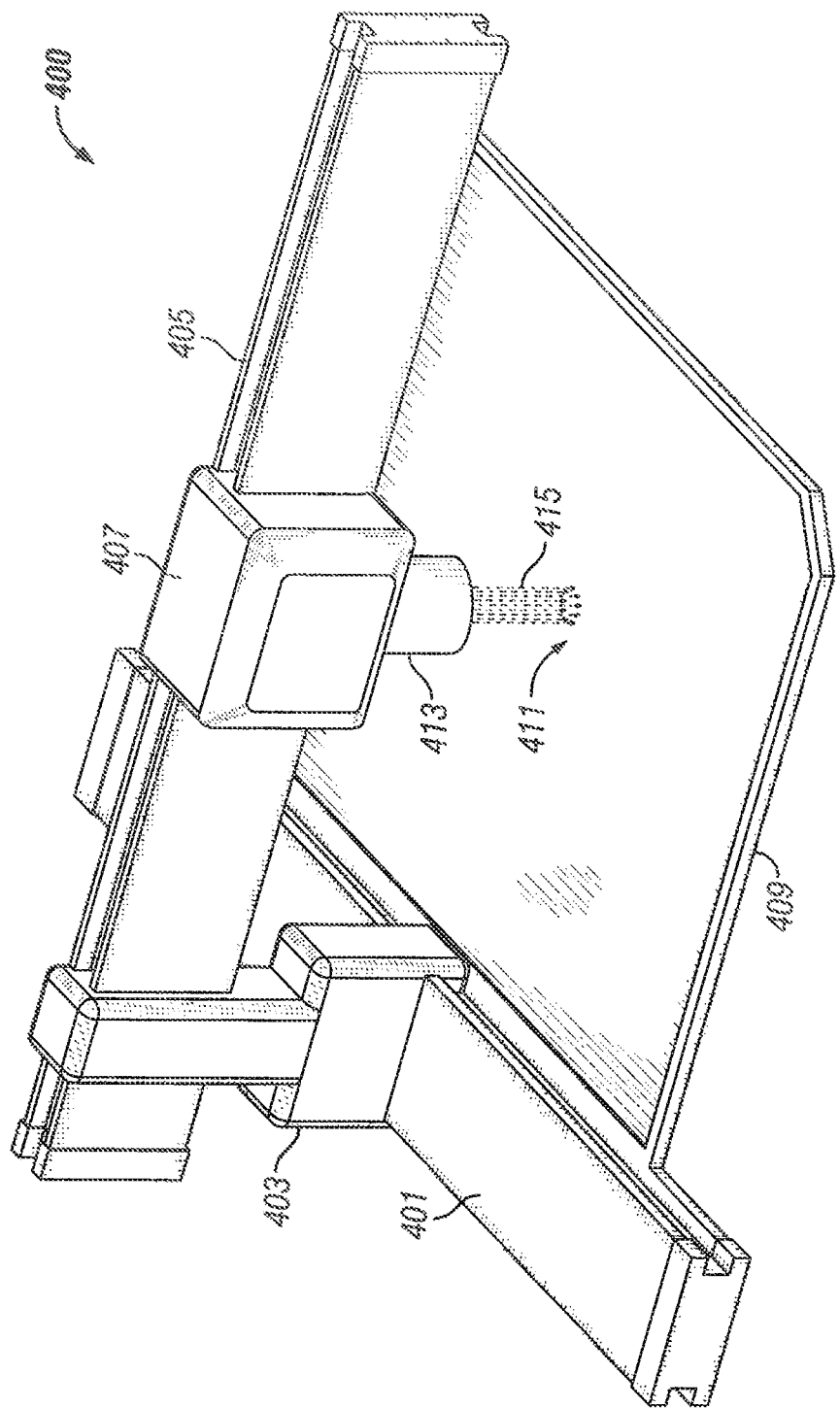
FIG. 4 is a perspective view illustrating an X-Y programmable scanning mechanism for use with an LLLT device or other light source device according to the present disclosure.

Referring now to FIG. 4, an X-Y programmable scanning mechanism for use with an LLLT device or other light source device according to the present disclosure is shown. An X-Y scanning mechanism 400 includes a base bar or rail 401 and an arm 405 positioned transversely to the base rail 401. The arm 405 is moveably mounted to the base rail 401 by a moveable mount 403. The arm 405 is moved back and forth along base rail 401, such as by sliding, for example, by a motor or other means (not shown) incorporated within moveable mount 403. A light source module 413 is moveably mounted to arm 405 by a moveable mount 407. Similarly, the light source module 413 is moved back and forth along arm 405, such as by sliding, for example, by a motor or other means (not shown) incorporated within moveable mount 407. X-Y scanner 400 is similar to an X-Y plotter that operates in two axes of motion ("X" and "Y") in order to define or draw continuous vector graphics. The base rail 401 can be treated as the "Y" axis, while the arm 405 is the "X" axis. As is known in the art, X-Y scanner 400 can be operated automatically by a computer programmed to continuously feed positioning commands to the motor or other means incorporated within moveable mounts 403 and 407 to move the light source module 413 in a desired pattern over the treatment area 411 to illuminate the treatment area at a predetermined distance. A frame 409 attached to the base rail 401 defines a treatment area 411.

As discussed above, light source module 413 may incorporate one or more light sources, such as one or more lasers (not shown) to provide a light beam 415. In one embodiment, the light source module 415 may incorporate a first laser that emits a beam having a wavelength of 635 nm, and a second laser that emits a beam having a wavelength of 808 nm. Light source module 413 then generates light beam 415 which includes light energy having both wavelengths. In another embodiment, as is known in the art, light source module 413 may incorporate three or more lasers having different wavelengths mounted in a cluster. In other embodiments, the light source module 413 may generate a greater or lesser number of light beams.

Figure 5A:
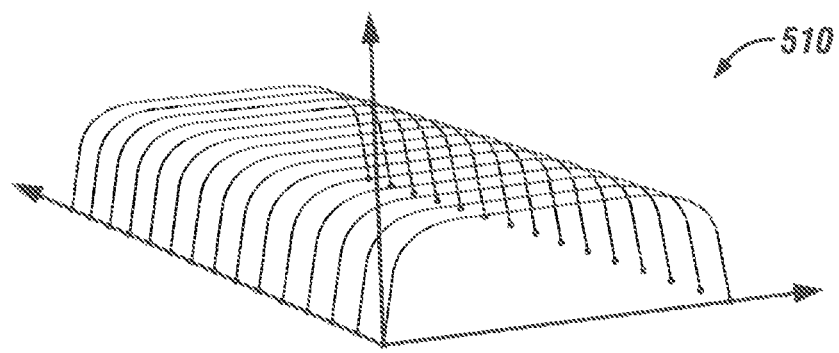
FIGS. 5A, 5B and 5C are a set of diagrams illustrating possible energy distribution patterns according to the present disclosure.
Figure 5B:
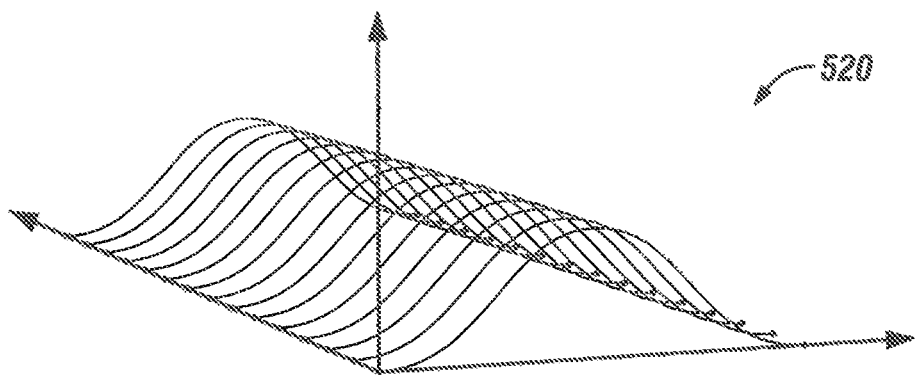
Figure 5C:
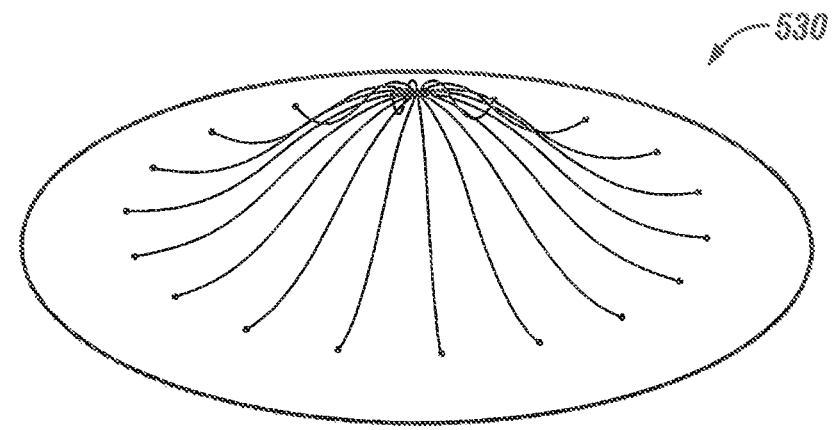

Referring now to FIG. 5, a set of graphs illustrating possible energy distribution patterns according to the present disclosure is shown. Using light source module 413 mounted to scanning mechanism 400, the light beam 415 can create a wide variety of desired energy distribution patterns at the surface of the treatment area 411, with each one of the wavelengths incorporated in the beam. Curve 510 illustrates a distribution that provides approximate equivalent energy to each area unit in the treatment area 411. Curve 520 illustrates an energy distribution for treatment of an elongated area such as a long scar or wound. Curve 530 illustrates a circular energy distribution at the treatment area 411.

Figure 6:
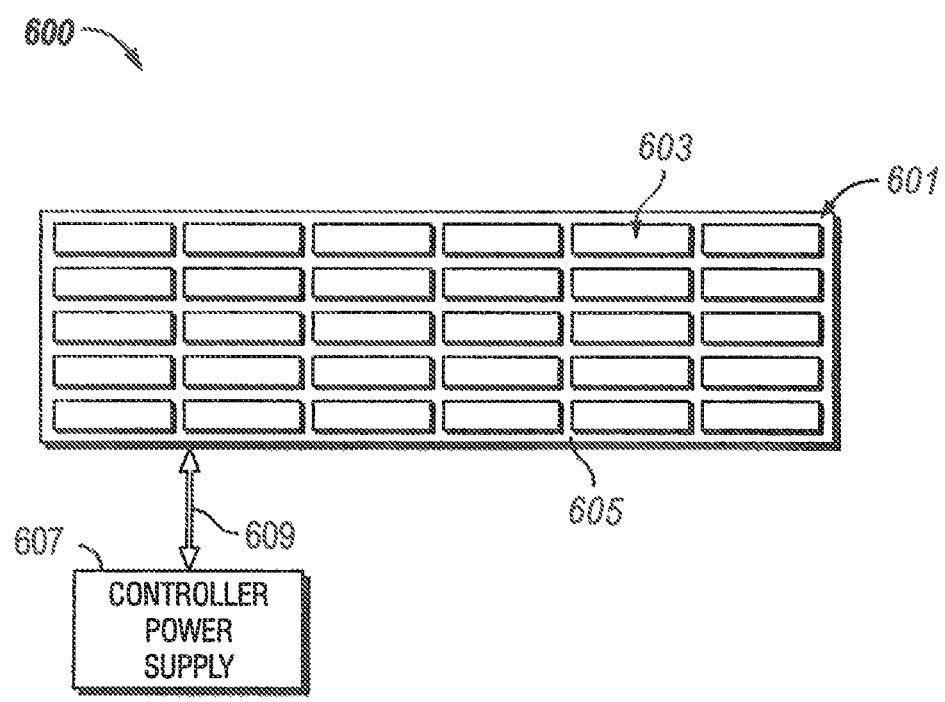
FIG. 6 is a diagram of an apparatus to manually create desired energy distribution patterns on a treatment area according to the present disclosure.

Referring now to FIG. 6, a diagram of an apparatus to manually create desired energy distribution patterns on a treatment area according to the present disclosure is shown. In another embodiment, an apparatus 600 enables a user to design and create desired or custom light source, such as low-level laser, for example, arrays to provide a desired energy distribution pattern on a treatment area (not shown). Such a light source array may be predetermined as a part of a standard LLLT treatment procedure, or the array may be a custom array designed during diagnosis of a patient to treat a specific ailment. A support frame 601, such as a flexible, semi-rigid belt or web, for example, includes an array of mounting points 603 to facilitate the mounting of one or more light source modules (not shown) at one or more of the mounting points 603 to form a desired array of light sources. Each of the light sources in the array includes optics to provide an array of parallel, coherent light beams to form the desired energy distribution pattern on the surface of a treatment area. Mounting points 603 may be slots or circular holes formed in support frame 601 or mounting brackets attached to support frame 601 at the mounting points 603, for example, or other suitable mounting apparatus. The housing 605 of support frame 601 includes electrical wiring, connections and other supporting circuitry to provide power for and control of the array of light source modules. While the support frame 601 is shown as a flat, rectangular plate, support frame 601 may also take other shapes and configurations, such as circular or square, for example, and may also be curved to attain the desired energy distribution pattern on a treatment area. A controller and power supply module 607 provides power and control signals to the array of light source modules via cabling 609.

The light source modules used to assemble the light source arrays may use lasers, such as diode lasers, for example, to generate the light beam. In some embodiments, the light source module will provide a monochromatic laser beam. In other embodiments, the light source module may incorporate two or more lasers, each generating a light beam having a different wavelength. In one embodiment, each light source module incorporates a pair of lasers, a first laser that emits a beam having a wavelength of 635 nm, and a second laser that emits a beam having a wavelength of 808 nm. In another embodiment, light source module includes a laser wherein the laser beam generated by the laser is shaped by using a lens to form a collimated elongated beam to cover a larger area, for example an area of 3-6 cm by 0.5 to 1 cm at the surface of the treatment area.

Support frame 601 may be mounted to a support structure (not shown) which maintains the light source module array positioned relative to a treatment area to provide the desired energy distribution pattern on a treatment area. Alternatively, support frame 601 may be mounted in a scanning mechanism such as the scanning mechanism 100 described above. Similarly, the support frame 601 may be mounted to moveable mount 407 in the X-Y scanner mechanism 400 described above.

In another embodiment, support frame 601 includes a light source module mounted at each of the mounting points 603 forming an array of light source modules. A controller and power supply module 607 provides power and control signals to the array of light source modules via cabling 609. The controller 607 is programmed to switch selected ones of the light sources on and off to provide predetermined energy distribution patterns on a treatment area.

While the methods and apparatus of the present application have been described in terms of various embodiments, it will be apparent to those of skill in the art that variations may be applied to the methods, apparatus and/or processes, and in the steps or in the sequence of steps of the methods described herein without departing from the concept and scope of the application. More specifically, it will be apparent that certain features which are both mechanically and functionally related may be substituted for the features described herein while the same or similar results would be achieved. All such similar substitutes and modifications apparent to those skilled in the art are deemed to be within the scope and concept of the application.

What is claimed is:

1. A low-level laser therapy apparatus comprising:
   a light source module comprising a body containing at least one low-level laser light diode and a lens, the diode being configured to produce light that diverges with an angle in a first direction and with a larger angle in a second perpendicular direction, the diode and lens being configured in combination to produce a collimated light beam elongated in a cross-section and exhibiting a wavelength within the range of greater than 600 to 1,000 nm, the light source module being configured to illuminate a treatment area of a surface with the collimated, elongated light beam, the treatment area being external to the light source module, the cross-section being taken in a plane perpendicular to an axis of the collimated, elongated light beam, and the collimated, elongated light beam rendering the cross-section approximately the same along the axis between the light source module and the treatment area; and
   a scanning mechanism attached to the body of the light source module and adapted to impart motion to the body of the light source module, thereby to impart the motion to the low-level laser light diode and the lens of the light source module as well, the motion being configured to produce an energy distribution in a unit area of the treatment area, the energy distribution differing from an energy distribution of the collimated, elongated light beam that exists in the unit area without any motion, the motion including at least rotation of the body of the light source module about the axis, the rotation of the body of the light source module producing a more uniform energy distribution in the unit area compared to the energy distribution of the collimated, elongated light beam in the unit area without any motion, and the unit area having a diameter equal to a long dimension of the collimated, elongated light beam cross-section as a result of the rotation.

2. The apparatus of claim 1, wherein the light source module further comprises a visible light source configured to emit a supplementary visible light beam.

3. The apparatus of claim 1, wherein the light source module comprises two or more light diodes configured in combination to produce a composite light beam of two or more individually collimated, coherent light beams, each of the two or more light diodes generating a light beam having a different wavelength.

4. The apparatus of claim 3, wherein each of the two or more light diodes exhibits a different energy distribution within the unit area of the treatment area.

5. The apparatus of claim 1, wherein the scanning mechanism is an X-Y scanner comprising:
   a base rail;
   an arm transversely positioned to the base rail, wherein the arm is moveably mounted to the base rail; and
   a mount attached to the light source module, wherein the mount is moveably mounted to the arm.

6. The apparatus of claim 5, further comprising a controller programmed to move the body of the light source module in different patterns to provide energy distribution patterns at the surface of a treatment area in accordance with a treatment procedure.

7. The apparatus of claim 1, where the light beam is coherent with a common phase.

8. The apparatus of claim 7, wherein the light source module has an average power falling within the range of 1 mW to 500 mW.

9. The apparatus of claim 8, wherein the light beam has a wavelength of 808 nm.

10. The apparatus of claim 9, wherein the scanning mechanism rotates the body of the light source module at a rate of 2 revolutions per minute.

11. A low-level laser therapy apparatus, comprising:
    a support frame;
    a plurality of mounting points formed in the support frame;
    at least one light source module mounted on the support frame at one or more of the mounting points, the at least one light source module including at least one low-level laser light diode configured to produce light that diverges with an angle in a first direction and with a larger angle in a second perpendicular direction, the light source module being configured to produce a collimated light beam elongated in a cross-section and exhibiting a wavelength within the range of greater than 600 to 1,000 nm and the apparatus being configured to illuminate a treatment area of a surface with the collimated, elongated light beam, the treatment area being external to the light source module, the cross-section being taken in a plane perpendicular to an axis of the collimated, elongated light beam, and the collimated, elongated light beam rendering the cross-section approximately the same along the axis between the light source module and the treatment area; and
    a scanning mechanism attached to the support frame and adapted to impart motion to the support frame, thereby to impart the motion to the low-level laser light diode of the light source module as well, the motion being configured to produce an energy distribution in a unit area of the treatment area, the energy distribution differing from an energy distribution of the collimated, elongated light beam that exists in the unit area without any motion, the motion including at least rotation of the support frame about the axis, the rotation of the support frame producing a more uniform energy distribution in the unit area compared to the energy distribution of the collimated, elongated light beam in the unit area without any motion, and the unit area having a diameter equal to a long dimension of the collimated, elongated light beam cross-section as a result of the rotation.

12. The apparatus of claim 11, wherein the mounting points comprise slots formed in the support frame.

13. The apparatus of claim 11, further comprising an array of a plurality of the light source modules mounted on the support frame at one or more of the mounting points in a predetermined pattern.

14. The apparatus of claim 13, further comprising a power supply module coupled to the support frame for providing control signals and power to the array of light source modules.

15. The apparatus of claim 11, wherein the light beam has a wavelength of 808 nm.

16. The apparatus of claim 11, wherein the support frame comprises a semi-rigid plate.

17. The apparatus of claim 11, further comprising a light source module mounted at each of the mounting points forming an array.

18. The apparatus of claim 11, further comprising a controller programmed to switch selected ones of the light source modules on and off to provide predetermined energy distribution patterns on a treatment area.

19. The apparatus of claim 1, wherein the light beam has a wavelength within the range of greater than 800 nm to 1000 nm.

20. The apparatus of claim 19, wherein the light source produces light having a divergence of 5 degrees to 7 degrees along its width and 30 degrees to 40 degrees along its length.

21. The apparatus of claim 11, wherein the scanning mechanism is an X-Y scanner comprising:
 a base rail;
 an arm transversely positioned to the base rail, wherein the arm is moveably mounted to the base rail; and
 a mount attached to the support frame, wherein the mount is moveably mounted to the arm.

22. The apparatus of claim 11, further comprising a controller programmed to move the support frame in different patterns to provide energy distribution patterns at the surface of a treatment area in accordance with a treatment procedure.

23. The apparatus of claim 11, wherein the light beam exhibits a wavelength within the range of greater than 800 nm to 1000 nm.

* * * * *